United States Patent [19]

Bourzat et al.

[11] 4,167,571
[45] Sep. 11, 1979

[54] THIAZOLINE DERIVATIVES

[75] Inventors: Jean D. Bourzat, Paris; Daniel Farge, Thiais; André Léger, Paris; Gerard Ponsinet, Sucy-en-Brie, all of France

[73] Assignee: Rhone-Poulenc Industries, Paris, France

[21] Appl. No.: 952,198

[22] Filed: Oct. 17, 1978

[30] Foreign Application Priority Data

Oct. 19, 1977 [FR] France ................................. 77 31431
Sep. 13, 1978 [FR] France ................................. 78 26304

[51] Int. Cl.² .................... C07D 417/04; A61K 31/44
[52] U.S. Cl. ...................................... 424/263; 546/280
[58] Field of Search .......................... 546/280; 424/263

[56] References Cited
U.S. PATENT DOCUMENTS 3,761,485  9/1973  Erdelyi et al. ...................... 546/280

Primary Examiner—Alan L. Rotman

Attorney, Agent, or Firm—Stevens, Davis, Miller & Mosher

[57] ABSTRACT

New thiazoline derivaties of the formula:

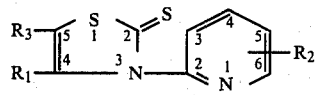

wherein $R_1$ represents hydrogen, an alkyl radical of 1 or 2 carbon atoms or methoxymethyl, $R_2$ represents an alkyl radical of 1 or 2 carbon atoms in the 4-, 5- or 6-position, and $R_3$ represents methyl, or alternatively $R_3$ represents hydrogen and either $R_1$ represents hydrogen, an alkyl radical of 1 through 4 carbon atoms, or an alkoxymethyl radical in which the alkyl moiety contains 1 through 4 carbon atoms, and $R_2$ represents an alkyl radical of 1 through 4 carbon atoms in the 4-, 5- or 6-position, or $R_1$ represents cyclopropyl and $R_2$ represents hydrogen are useful as medicaments and, more particularly, as anti-ulcer agents.

21 Claims, No Drawings

THIAZOLINE DERIVATIVES

DESCRIPTION

This invention relates to new therapeutically useful thiazoline derivatives of the general formula:

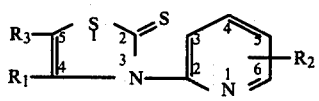

wherein (a) $R_1$ represents a hydrogen atom or an alkyl radical containing 1 or 2 carbon atoms, or a methoxymethyl radical, $R_2$ represents an alkyl radical containing 1 or 2 carbon atoms in the 4-, 5- or 6-position, and $R_3$ represents a methyl radical, or alternatively (b) $R_3$ represents a hydrogen atom and either $R_1$ represents a hydrogen atom, a straight- or branched-chain alkyl radical containing 1 to 4 carbon atoms, or an alkoxymethyl radical in which the alkyl moiety contains 1 to 4 carbon atoms in a straight or branched chain, and $R_2$ represents a straight- or branched-chain alkyl radical containing 1 to 4 carbon atoms in the 4-, 5- or 6-position, or $R_1$ represents a cyclopropyl radical and $R_2$ represents a hydrogen atom.

According to a feature of the present invention, the thiazoline derivatives of general formula I are prepared by the process which comprises dehydrating a compound of the general formula:

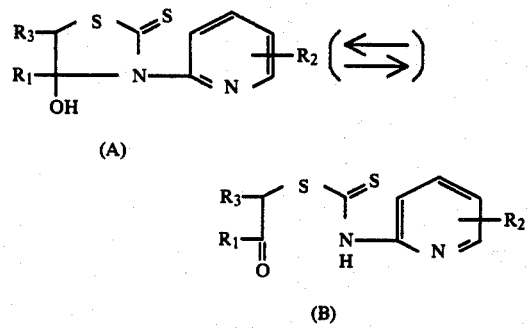

wherein $R_1$, $R_2$ and $R_3$ are as hereinbefore defined.

The general formula IIA generally corresponds to the preponderant form, in the crystalline state, of the products in which $R_1$, $R_2$ and $R_3$ are as defined above under (a), or alternatively $R_3$ represents a hydrogen atom and either $R_1$ represents a hydrogen atom, an alkyl radical containing 1 to 4 carbon atoms, the carbon atoms of which are primary or secondary, or an alkoxymethyl radical in which the alkyl moiety contains 1 to 4 carbon atoms in a straight or branched chain and $R_2$ represents an alkyl radical containing 1 to 4 carbon atoms in the 4-, 5- or 6-position, or $R_1$ represents a cyclopropyl radical and $R_2$ represents a hydrogen atom.

The general formula IIB generally corresponds to the preponderant form, in the crystalline state, of the products in which $R_1$ represents a tert.-butyl radical, $R_2$ represents an alkyl radical containing 1 to 4 carbon atoms in the 4-, 5- or 6-position, and $R_3$ represents a hydrogen atom.

The dehydration of compounds of general formula II is advantageously carried out in a strong inorganic or organic acid medium at a temperature between 60° C. and the reflux temperature of the reaction mixture. The reaction is preferably carried out in the presence of p-toluenesulphonic acid in an organic solvent such as toluene, or in the presence of a methanolic solution of hydrochloric acid.

The compounds of general formula II can be obtained by the reaction of an α-halogen-ketone or -aldehyde of the general formula:

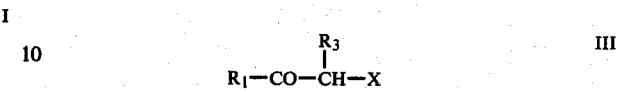

(wherein $R_1$ and $R_3$ are as hereinbefore defined, and X represents a halogen, preferably a bromine or chlorine, atom) with a dithiocarbamate of the general formula:

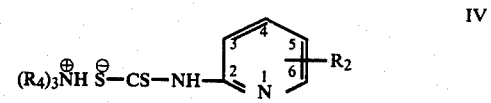

wherein $R_2$ is as hereinbefore defined and the symbols $R_4$ (which are identical or different) each represent an alkyl radical containing 1 to 4 carbon atoms.

The reaction of a compound of general formula III with a dithiocarbamate of the general formula IV is generally carried out in an organic solvent (for example dimethylformamide or acetonitrile), in water, or in an aqueous-organic medium (for example a mixture of water and acetonitrile) at a temperature between −10° and +50° C. It is not essential to isolate the resulting compound of general formula II from the reaction mixture in order to carry out the dehydration.

The dithiocarbamates of the general formula IV can be obtained in accordance with the method described by E. B. Knott, J. Chem. Soc., 1644–9 (1956), or in accordance with German Patent Application DE No. 2508891, by the action of carbon disulphide, in the presence of a tertiary amine, on a 2-aminopyridine of the general formula:

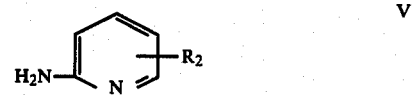

wherein $R_2$ is as hereinbefore defined.

The thiazoline derivatives of general formula I so obtained can optionally be purified by physical methods such as crystallization or chromatography.

The thiazoline derivatives of general formula I possess pharmacological properties which justify their use as anti-ulcer agents.

The compounds of general formula I have shown themselves to be active as anti-ulcer agents in rats at doses of between 5 and 100 mg/kg animal body weight, administered orally, using the technique of Rossi et al., C. R. Soc. Biol., 150, 2124, and some of them have shown themselves to be active at the same doses using the technique of Shay et al., Gastroenterology, 5, 43 (1945). Some of them have also shown themselves to be active as anti-ulcer agents in guinea pigs at doses of between 5 and 100 mg/kg animal body weight, administered orally, using the technique of Anderson and Watt, J. Physiol. (London), 147, 52 P (1959).

The acute toxicity of the compounds of the invention, expressed as a 50% lethal dose ($LD_{50}$) in the case of mice is between 100 and more than 900 mg/kg animal body weight administered orally.

Of particular interest are the thiazoline derivatives of general formula I wherein $R_1$ represents an alkyl radical containing 1 to 4 carbon atoms, or a methoxymethyl radical, $R_2$ represents an alkyl radical containing 1 to 4 carbon atoms in the 4-, 5- or 6-position, and $R_3$ represents a hydrogen atom, and especially those such compounds of general formula I wherein $R_1$ represents an alkyl radical containing 1 or 2 carbon atoms, or a methoxymethyl radical, $R_2$ represents an alkyl radical containing 1 to 4 carbon atoms in the 4-, 5- or 6-position, and $R_3$ represents a hydrogen atom.

Compounds of outstanding interest for their good anti-ulcer activity are 4-methyl-3-(4-methylpyrid-2-yl)-$\Delta^4$-thiazoline-2-thione, 4-methyl-3-(6-methylpyrid-2-yl)-$\Delta^4$-thiazoline-2-thione, 3-(6-ethylpyrid-2-yl)-4-methyl-$\Delta^4$-thiazoline-2-thione, 4-ethyl-3-(6-methylpyrid-2-yl)-$\Delta^4$-thiazoline-2-thione, 4-methoxymethyl-3-(6-methylpyrid-2-yl)-$\Delta^4$-thiazoline-2-thione and 4-methyl-3-(6-propylpyrid-2-yl)-$\Delta^4$-thiazoline-2-thione.

The following non-limitative Examples illustrate the preparation of thiazoline derivatives of the present invention.

EXAMPLE 1

2-Chloro-1-cyclopropylethan-1-one (22.5 g) is added, at between 15° and 20° C., to a suspension of triethylammonium pyrid-2-yldithiocarbamate (51.5 g) in anhydrous acetonitrile (500 cc). The reaction is allowed to proceed for 3 hours at 20°–25° C. The reaction mixture is then evaporated to dryness under reduced pressure (20 mm Hg) at 40° C. The evaporation residue is dissolved in a mixture of ethyl acetate (1000 cc) and distilled water (1000 cc). After stirring and decantation, the organic phase is washed twice with distilled water (total 250 cc), dried over sodium sulphate and evaporated under reduced pressure (20 mm Hg) at 40° C.

The product obtained (46.1 g) is dissolved in a boiling mixture of diisopropyl ether (1200 cc) and acetonitrile (230 cc). Decolourising charcoal (2 g) is added to the boiling solution, the mixture is then filtered at the boil and the filtrate is allowed to cool for 2 hours at 2° C. The resulting crystals are filtered off, washed twice with diisopropyl ether (total 150 cc) and dried under reduced pressure (0.2 mm Hg) at 40° C. 4-Cyclopropyl-4-hydroxy-3-(pyrid-2-yl)-thiazolidine-2-thione (30.8 g), melting at 95° C., is thus obtained.

A mixture of 4-cyclopropyl-4-hydroxy-3-(pyrid-2-yl)-thiazolidine-2-thione (18.4 g), methanol (200 cc) and a 12 N aqueous solution of hydrochloric acid (2 cc) is heated under reflux for 30 minutes. The reaction mixture is then cooled to 40° C. and evaporated to dryness under reduced pressure (20 mm Hg) at 40° C. The evaporation residue is treated with a 10% aqueous solution of sodium bicarbonate (100 cc); the insoluble material is extracted three times with chloroform (total 200 cc), the combined organic extracts are washed twice with distilled water (total 100 cc), dried over sodium sulphate and evaporated under reduced pressure (20 mm Hg) at 40° C.

The product obtained (24.1 g) is dissolved in a boiling mixture of diisopropyl ether (350 cc) and acetonitrile (20 cc). Decolourising charcoal (1 g) is added to the boiling solution, the mixture is then filtered at the boil and the filtrate is allowed to cool for 2 hours at 2° C. The resulting crystals are filtered off, washed twice with diisopropyl ether (total 100 cc) and dried under reduced pressure (0.2 mm Hg) at 40° C. 4-Cyclopropyl-3-(pyrid-2-yl)-$\Delta^4$-thiazoline-2-thione (11.3 g), melting at 93° C., is thus obtained.

2-Chloro-1-cyclopropylethan-1-one (b.p. 67° C./20 mm Hg) is prepared in accordance with the method described by E. M. Kosower et al., J. Org. Chem., 28, 630–3 (1963). Triethylammonium pyrid-2-yldithiocarbamate is prepared in accordance with the method described by E. B. Knott, J. Chem. Soc., 1644–9 (1956).

EXAMPLE 2

A 50% aqueous solution of chloroacetaldehyde (28.4 g) is added, at between 20° and 30° C., to a solution of triethylammonium 6-methylpyrid-2-yldithiocarbamate (51.5 g) in distilled water (225 cc). The reaction mixture is stirred for 2 hours at 25° C. The crude product is filtered off, washed five times with distilled water (total 125 cc) and dried in air. The product obtained (37.0 g; m.p. 128° C.) is dissolved in boiling ethanol (250 cc). After filtering the boiling solution and cooling the filtrate for 2 hours at 2° C., the resulting crystals are filtered off, washed three times with ice-cooled ethanol (total 30 cc) and dried under reduced pressure (0.2 mm Hg) at 40° C. 4-Hydroxy-3-(6-methylpyrid-2-yl)-thiazolidine-2-thione (29.8 g), melting at 128° C., is thus obtained.

A solution of 4-hydroxy-3-(6-methylpyrid-2-yl)-thiazolidine-2-thione (21.0 g) in methanol (210 cc) is heated under reflux for 5 hours in the presence of a 12 N aqueous solution of hydrochloric acid (8.0 cc). The methanol is evaporated off and the reaction products are then treated with an N aqueous solution of sodium hydroxide (100 cc); the insoluble oil is extracted with methylene chloride (300 cc) and then with diethyl ether (150 cc). The combined organic extracts are washed twice with distilled water (total 200 cc), dried over sodium sulphate, treated with decolourising charcoal (1.0 g) and evaporated. The product obtained (17.5 g) is dissolved in boiling ethanol (40 cc). After cooling for 2 hours at 2° C., the resulting crystals are filtered off, washed twice with ice-cooled ethanol (total 10 cc) and then with diisopropyl ether (10 cc) and dried under reduced pressure (0.2 mm Hg) at 40° C. 3-(6-Methylpyrid-2-yl)-$\Delta^4$-thiazoline-2-thione (10.1 g), melting at 85° C., is thus obtained.

Triethylammonium 6-methylpyrid-2-yldithiocarbamate is prepared in accordance with the method described by E. B. Knott, J. Chem. Soc., 1644–9 (1956).

EXAMPLE 3

Chloroacetone (32.3 g) is added, at 20° C., to a solution of triethylammonium 4-methylpyrid-2-yldithiocarbamate (100 g) in dimethylformamide (450 cc). The reaction mixture is stirred at 20° C. for 1 hour. The triethylammonium chloride formed is removed by filtering the reaction mixture and washed with dimethylformamide (60 cc). The dimethylformamide is evaporated off under reduced pressure (0.1 mm Hg) at 50° C., the residual oil is then taken up in methylene chloride (700 cc) and the solution thus obtained is washed twice with distilled water (total 300 cc), dried over sodium sulphate and evaporated to dryness under reduced pressure (20 mm Hg) at 20° C. The oily residue is dissolved in a boiling mixture of ethanol (250 cc) and diisopropyl ether (250 cc). After cooling for 2 hours at 2° C., the resulting crystals are filtered off, washed twice with an ice-cooled mixture (total 20 cc) of ethanol (10 cc) and diisopropyl ether (10 cc) and dried under reduced pressure (20 mm Hg) at 45° C. 4-Hydroxy-4-methyl-3-(4-methylpyrid-2-yl)-thiazolidine-2-thione (49.0 g), melting at 119° C., is thus obtained.

A mixture of 4-hydroxy-4-methyl-3-(4-methylpyrid-2-yl)-thiazolidine-2-thione (25 g), toluene (500 cc) and p-toluenesulphonic acid monohydrate (2.5 g) is heated under reflux for 5 hours. The reaction mixture is subsequently cooled to 20° C. and then treated with a 10% solution of sodium bicarbonate (200 cc). The organic phase is decanted, washed with distilled water (200 cc), dried over sodium sulphate and evaporated to dryness under reduced pressure (20 mm Hg) at 40° C.

The product obtained (28 g, m.p. 120° C.) is dissolved in boiling ethanol (120 cc) and decolourising charcoal (1 g) is then added. After filtering the boiling solution and cooling of the filtrate for 2 hours at 2° C., the resulting crystals are filtered off, washed twice with ice-cooled ethanol (total 20 cc) and dried under reduced pressure (0.1 mm Hg) at 45° C. 4-Methyl-3-(4-methylpyrid-2-yl)-$\Delta^4$-thiazoline-2-thione (23.1 g), melting at 129° C., is thus obtained.

Triethylammonium 4-methylpyrid-2-yldithiocarbamate is prepared in accordance with the method described by E. B. Knott, J. Chem. Soc., 1644–9 (1956).

EXAMPLE 4

A solution of triethylammonium 5-methylpyrid-2-yldithiocarbamate (75 g) in dimethylformamide (340 cc) is reacted, at 20° C., with chloroacetate (20.9 cc). The reaction mixture is stirred for 16 hours at 20° C. The triethylammonium chloride formed is removed by filtering the reaction mixture and washed with dimethylformamide (50 cc). The dimethylformamide is evaporated off under reduced pressure (0.1 mm Hg) at 50° C., the residual oil is then taken up in methylene chloride (700 cc) and the solution thus obtained is washed twice with distilled water (total 200 cc), dried over sodium sulphate and evaporated to dryness under reduced pressure (20 mm Hg) at 20° C. The oily residue is taken up in a mixture of ethanol (100 cc) and diisopropyl ether (150 cc) and then treated with decolourising charcoal (1 g) and heated to the boiling point. After filtering the boiling solution and cooling the filtrate for 2 hours at 2° C., the resulting crystals are filtered off, washed twice with an ice-cooled mixture (total 50 cc) of ethanol (20 cc) and diisopropyl ether (30 cc), and dried under reduced pressure (0.1 mm Hg) at 20° C. 4-Hydroxy-4-methyl-3-(5-methylpyrid-2-yl)-thiazolidine-2-thione (45.1 g), melting at 113° C., is thus obtained.

The procedure of Example 3 is then followed but 4-hydroxy-4-methyl-3-(5-methylpyrid-2-yl)-thiazolidine-2-thione (15 g) and p-toluenesulphonic acid monohydrate (1.5 g) in toluene (300 cc) are used as the starting materials. After recrystallisation of the product from ethanol, 4-methyl-3-(5-methylpyrid-2-yl)-$\Delta^4$-thiazoline-2-thione (10.0 g), melting at 108° C., is obtained.

Triethylammonium 5-methylpyrid-2-yldithiocarbamate is prepared in accordance with the method described in German Patent Application DE No. 2508891.

EXAMPLE 5

By following the procedure of Example 4 but using triethylammonium 6-methylpyrid-2-yldithiocarbamate (43 g) and chloroacetone (13.9 cc) in dimethylformamide (250 cc) as the starting materials, 4-hydroxy-4-methyl-3-(6-methylpyrid-2-yl)-thiazolidine-2-thione (24.9 g), melting at 156° C., is obtained after recrystallisation from ethanol.

The procedure of Example 3 is then followed but 4-hydroxy-4-methyl-3-(6-methylpyrid-2-yl)-thiazolidine-2-thione (15 g) and p-toluenesulphonic acid monohydrate (1.5 g) on toluene (300 cc) are used as the starting materials. After recrystallisation of the product from ethanol, 4-methyl-3-(6-methylpyrid-2-yl)-$\Delta^4$-thiazoline-2-thione (9.1 g), melting at 125° C., is obtained.

EXAMPLE 6

By following the procedure of Example 2 but using triethylammonium 6-ethylpyrid-2-yldithiocarbamate (43.5 g) and 1-chloropropan-2-one (13.4 g) in distilled water (220 cc) as the starting materials, 3-(6-ethylpyrid-2-yl)-4-hydroxy-4-methylthiazolidine-2-thione (25.5 g), melting at 122° C., is obtained after recrystallisation from ethanol (120 cc).

A solution of 3-(6-ethylpyrid-2-yl)-4-hydroxy-4-methylthiazolidine-2-thione (12.8 g) in methanol (125 cc) is heated under reflux for 15 minutes in the presence of a 12 N aqueous solution of hydrochloric acid (5.0 cc). After stirring for a further 2 hours at 25° C., the procedure of Example 2 is followed and 3-(6-ethylpyrid-2-yl)-4-methyl-$\Delta^4$-thiazoline-2-thione (9.8 g), melting at 91° C., is obtained after recrystallisation of the product from ethanol (33 cc).

Triethylammonium 6-ethylpyrid-2-yldithiocarbamate can be prepared in the following manner:

A solution of carbon disulphide (17.5 cc) in anhydrous acetonitrile (19.5 cc) is added, at 25° C., to a solution of 2-amino-6-ethylpyridine (27.0 g) in anhydrous triethylamine (60 cc). After stirring for 20 hours at 20° C., anhydrous diethyl ether (250 cc) is added. After cooling for 1 hour at 2° C., the resulting crystals are filtered off, washed three times with anhydrous diethyl ether (total 240 cc) and dried under reduced pressure (20 mm Hg) at 20° C. Triethylammonium 6-ethylpyrid-2-yldithiocarbamate (42.0 g), melting at 75° C., is thus obtained.

2-Amino-6-ethylpyridine is prepared in accordance with the method described by S. J. Childress and J. V. Scusi, J. Org. Chem., 23, 68 (1958).

EXAMPLE 7

By following the procedure of Example 2 but using triethylammonium 6-methylpyrid-2-yldithiocarbamate (71.0 g) and 1-chlorobutan-2-one (26.6 g) in distilled water (300 cc) as the starting materials, 4-ethyl-4-hydroxy-3-(6-methylpyrid-2-yl)-thioazolidine-2-thione (45.0 g), melting at 118° C., is obtained after recrystallisation from ethanol (250 cc).

A solution of 4-ethyl-4hydroxy-3-(6-methylpyrid-2-yl)-thiazolidine-2-thione (25.4 g) in methanol (250 cc) is heated under reflux for 15 minutes in the presence of a 12 N aqueous solution of hydrochloric acid (5.0 cc). By following the procedure of Example 2, 4-ethyl-3-(6-methylpyrid-2-yl)-$\Delta^4$-thiazoline-2-thione (21.6 g), melting at 148° C., is then obtained after recrystallisation of the product from ethanol (250 cc).

1-Chlorobutan-2-one is prepared in accordance with the method described by P. J. Ashworth et al., J. Chem. Soc., 4633 (1957).

EXAMPLE 8

The procedure of Example 1 is followed but triethylammonium 6-ethylpyrid-2-yldithiocarbamate (72.0 g) and 1-chlorobutan-2-one (25.5 g) in anhydrous acetonitrile (400 cc) are used as the starting materials, and the reaction is initiated at between 20° and 25° C. The reaction is allowed to proceed for 16 hours at 20° C.

The crude product obtained (57.0 g) is purified by a first recrystallisation from ethanol (120 cc); a light brown solid (47 g) is thus obtained and is dissolved in chloroform (300 cc) and the solution is filtered through silica (0.02–0.063 mm; 470 g) contained in a column 5.5 cm in diameter. Elution is carried out with chloroform (5.0 liters). The solvent is evaporated under reduced pressure (20 mm Hg) at 40° C. and the product obtained (43.0 g) is then recrystallised again from ethanol (120 cc). 4-Ethyl-3-(6-ethylpyrid-2-yl)-4-hydroxythiazolidine-2-thione (37.2 g), melting at 84° C., is obtained.

Dehydration is carried out as described in Example 1 but using 4-ethyl-3-(6-ethylpyrid-2-yl)-4-hydroxy-thiazolidine-2-thione (21.6 g), methanol (240 cc) and a 12 N aqueous solution of hydrochloric acid (3 cc) as the starting materials. The reaction is allowed to proceed for 1 hour at the reflux temperature of methanol. After recrystallisation of the product from ethanol (70 cc), 4-ethyl-3-(6-ethylpyrid-2-yl)-$\Delta^4$-thiazolidine-2-thione (19.5 g), melting at 105° C., is obtained.

1-Chlorobutan-2-one (b.p. 119°–122° C./760 mm Hg) is prepared in accordance with the method described by P. J. Ashworth et al., J. Chem. Soc., 4633 (1957).

EXAMPLE 9

The procedure of Example 1 is followed but triethylammonium 6-methylpyrid-2-yldithiocarbamate (28.5 g) and 1-chloropentan-2-one (12.1 g) in anhydrous acetonitrile (200 cc) are used as the starting materials, and the reaction is initiated at between 15° and 25° C. The reaction is allowed to proceed for 2 hours at 20°–25° C. After recrystallisation from cyclohexane (500 cc), 4-hydroxy-3-(6-methylpyrid-2-yl)-4-propyl-thiazolidine-2-thione (21.6 g), melting at 83° C., is obtained.

Dehydration is carried out as described in Example 1 but 4-hydroxy-3-(6-methylpyrid-2-yl)-4-propylthiazolidine-2-thione (17.9 g), methanol (180 cc) and a 12 N aqueous solution of hydrochloric acid (3 cc) are used as the starting materials. The reaction is allowed to proceed for 1 hour at the reflux temperature of methanol. After recrystallisation of the product from diisopropyl ether (600 cc), 3-(6-methylpyrid-2-yl)-4-propyl-$\Delta^4$-thiazoline-2-thione (13.5 g), melting at 98° C., is obtained.

Triethylammonium 6-methylpyrid-2-yldithiocarbamate is prepared in accordance with the method described by E. B. Knott, J. Chem. Soc., 1644–9 (1956).

1-Chloropentan-2-one (b.p. 65°–67° C./30 mm Hg) is prepared in accordance with the method described by R. D. Haworth et al., J. Chem. Soc., 3617 (1954).

EXAMPLE 10

The procedure of Example 1 is followed but triethylammonium 6-methylpyrid-2-yldithiocarbamate (34.2 g) and 1-chlorohexan-2-one (16.1 g) in anhydrous acetonitrile (300 cc) are used as the starting materials, and the reaction is initiated at between 20° and 25° C. The reaction is allowed to proceed for 2 hours at 20° C. After recrystallisation from cyclohexane (600 cc), 4-butyl-4-hydroxy-3-(6-methylpyrid-2-yl)-thiazolidine-2-thione (28.3 g), melting at 80° C., is obtained.

Dehydration is carried out as described in Example 1 but 4-butyl-4-hydroxy-3-(6-methylpyrid-2-yl)-thiazolidine-2-thione (13.0 g), methanol (150 cc) and a 12 N aqueous solution of hydrochloric acid (3 cc) are used as the starting materials. The reaction is allowed to proceed for 1 hour at the reflux temperature of methanol. After recrystallisation of the product from a mixture of diisopropyl ether (300 cc) and acetonitrile (30 cc), 4-butyl-3-(6-methylpyrid-2-yl)-$\Delta^4$-thiazoline-2-thione (10.5 g), melting at 93° C., is obtained.

1-Chlorohexan-2-one (b.p. 80°–81° C./25 mm Hg) is prepared in accordance with the method described by H. Erlenmeyer and J. P. Jong, Helv. Chim. Acta. 32, 35 (1949).

EXAMPLE 11

The procedure of Example 1 is followed but triethylammonium 6-methylpyrid-2-yldithiocarbamate (28.5 g) and 1-chloro-4-methylpntan-2-one (13.4 g) in anhydrous acetonitrile (200 cc), are used as the starting materials and the reaction is initiated at between 20° and 25° C. The reaction is allowed to proceed for 2 hours at 20° C. After two successive recrystallisations from diisopropyl ether (300 cc), 4-hydroxy-4-isobutyl-3-(6-methylpyrid-2-yl)-thiazolidine-2-thione (16.8 g), melting at 95° C., is obtained.

Dehydration is carried out as described in Example 1 but 4-hydroxy-4-isobutyl-3-(6-methylpyrid-2-yl)-thiazolidine-2-thione (14.0 g), methanol (200 cc) and a 12 N aqueous solution of hydrochloric acid (3 cc) are used as the starting materials. The reaction is allowed to proceed for 3 hours at the reflux temperature of the methanol. After recrystallisation of the product from cyclohexane (250 cc), 4-isobutyl-3-(6-methylpyrid-2-yl)-$\Delta^4$-thiazoline-2-thione (10.3 g), melting at 90° C., is obtained.

1-Chloro-4-methylpentan-2-one (b.p. 72°–73° C./25 mm Hg) is prepared in accordance with the method described by F. Asinger et al., Ann. Chem., 672, 156 (1964).

EXAMPLE 12

The procedure of Example 1 is followed but triethylammonium 6-methylpyrid-2-yldithiocarbamate (46.5 g) and 3-chloro-1-methoxypropan-2-one (20.0 g) in anhydrous acetonitrile (350 cc) are used as the starting materials, and the reaction is initiated at between 15° and 20° C. The reaction is allowed to proceed for 3 hours at 20° C. After recrystallisation from ethanol (250 cc), 4-hydroxy-4-methoxymethyl-3-(6-methylpyrid-2-yl)-thiazolidine-2-thione (39.0 g), melting at 128° C., is obtained.

Dehydration is carried out as described in Example 1 but 4-hydroxy-4-methoxymethyl-3-(6-methylpyrid-2-yl)-thiazolidine-2-thione (20.0 g), methanol (150 cc) and a 12 N aqueous solution of hydrochloric acid (30 cc) are used as the starting materials. The reaction is allowed to proceed for 5 hours at the reflux temperature of the methanol. After recrystallisation of the product from ethanol (100 cc), 4-methoxymethyl-3-(6-methylpyrid-2-yl)-$\Delta^4$-thiazoline-2-thione (13.0 g), melting at 113° C., is obtained.

3-Chloro-1-methoxypropan-2-one (b.p. 84°–85° C./25 mm Hg) is prepared in accordance with the method described by B. G. Christensen et al., German Patent Application DE No. 2318829.

Triethylammonium 6-methylpyrid-2-yldithiocarbamate is prepared in accordance with the method described by E. B. Knott, J. Chem. Soc., 1644–9 (1956).

EXAMPLE 13

3-Chlorobutan-2-one (16.8 g) is added, at between 15° and 20° C., to a solution of triethylammonium 6-methyl-pyrid-2-yldithiocarbamate (47.0 g) in distilled water (250 cc). The reaction is allowed to proceed for 16 hours at 20°-25° C. and the resulting crystals are then filtered off, washed twice with distilled water (total 100 cc) and dried in the atmosphere.

The product obtained (49.0 g) is dissolved in boiling ethanol (210 cc). Decolourising charcoal (2 g) is added to the boiling solution, the mixture is filtered at the boil and the filtrate is allowed to cool for 2 hours at 2° C. The crystals which have appeared are filtered off, washed twice with ice-cooled ethanol (total 50 cc) and dried under reduced pressure (0.2 mm Hg) at 55° C. 4-Hydroxy-4,5-dimethyl-3-(6-methylpyrid-2-yl)-thiazolidine-2-thione (24.6 g), melting at 129° C., is thus obtained.

A mixture of 4-hydroxy-4,5-dimethyl-3-(6-methylpyrid-2-yl)-thiazolidine-2-thione (10.0 g), methanol (200 cc) and a 12 N aqueous solution of hydrochloric acid (1 cc) is stirred for 16 hours at 20°-25° C. The methanol is evaporated under reduced pressure (20 mm Hg) at 45° C. The residue is dissolved in chloroform (200 cc). The chloroform solution is washed with a 10% aqueous solution of sodium bicarbonate (70 cc) and then with distilled water (70 cc), dried over anhydrous sodium sulphate and evaporated. The product obtained (9.8 g) is dissolved in boiling ethanol (160 cc) and the boiling solution is filtered. After cooling the filtrate for 2 hours at 2° C., the resulting crystals are filtered off, washed with ice-cooled ethanol (20 cc) and dried under reduced pressure (0.2 mm Hg) at 45° C. 4,5-Dimethyl-3-(6-methylpyrid-2-yl)-$\Delta^4$-thiazoline-2-thione (7.8 g), melting at 166° C. is thus obtained.

EXAMPLE 14

The procedure of Example 1 is followed but triethylammonium 6-propylpyrid-2-yldithiocarbamate (50.0 g) and chloroacetone (15.3 g) in acetonitrile (500 cc) are used as the starting materials, and the reaction is initiated at between 20° and 28° C. The reaction is allowed to proceed for 2 hours at 20°-25° C. After recrystallisation from diisopropyl ether (80 cc), 4-hydroxy-4-methyl-3-(6-propylpyrid-2-yl)-thiazolidine-2-thione (32.2 g), melting at 68° C., is obtained.

Dehydration is carried out as described in Example 1 but 4-hydroxy-4-methyl-3-(6-propylpyrid-2-yl)-thiazolidine-2-thione (15.0 g), methanol (150 cc) and a 12 N aqueous solution of hydrochloric acid (2.2 cc) are used as the starting materials. The reaction is allowed to proceed for 2 hours at the reflux temperature of methanol. The solvent is evaporated under reduced pressure (20 mm Hg) at a maximum temperature of 40° C. and the residual oil is treated with ethyl acetate (300 cc). The organic solution is washed with a 5% aqueous solution of sodium bicarbonate (100 cc) and then with distilled water (50 cc), dried over sodium sulphate and evaporated. After drying the resulting oil under reduced pressure (0.1 mm Hg) at 40° C., 4-methyl-3-(6-propylpyrid-2-yl)-$\Delta^4$-thiazoline-2-thione (13.1 g) is obtained.

NMR spectrum (60 MHz) taken from a solution of about 10% in deuterated chloroform:
1.0 ppm: triplet (3H) J=7.5—CH$_3$ (chain)
1.8 ppm: sextet (2H) J=7.5—CH$_2$— (chain)
2.05 ppm: doublet (3H) J=1—CH$_3$ (heterocyclic ring)
2.88 ppm: triplet (2H) J=7.5—CH$_2$— (heterocyclic ring)
6.4 ppm: quartet (1H) J=1—H (heterocyclic ring)
7.32 ppm: DD (1H) J=7.5 and 0.5 —H(5-position)
7.35 ppm: DD (1H) J=7.5 and 0.5 —H(3-position
7.90 ppm: triplet (1H) J=7.5 —H(4-position).

Triethylammonium 6-propylpyrid-2-yldithiocarbamate can be prepared in the following manner:

A solution of carbon disulphide (20 cc) in anhydrous acetonitrile (23 cc) is added, at 20° C., to a solution of 2-amino-6-propylpyridine (34.0 g) in anhydrous triethylamine (69 cc). After stirring of the mixture for 20 hours at 20° C., anhydrous diethyl ether (800 cc) is added. After cooling for 1 hour at 2° C., the resulting crystals are filtered off, washed three times with anhydrous diethyl ether (total 300 cc) and dried under reduced pressure (20 mm Hg) at 20° C. Triethylammonium 6-propylpyrid-2-yldithiocarbamate (50.3 g), melting at about 98° C., is obtained.

2-Amino-6-propylpyridine is prepared in accordance with the method described by C. A. Salemink, Rec. Trav. Chim., 80, 552 (1961).

The present invention also includes within its scope pharmaceutical compositions which comprise, as active ingredient, a thiazoline derivative of general formula I in association with a pharmaceutically-acceptable carrier or coating. The invention includes especially such preparations made up for oral, parenteral or rectal administration.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Preparations according to the invention for parenteral administration include sterile suspensions or emulsions and non-aqueous solutions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilised by, for example, filtration through a bacteria-retaining filter, by incorporation in the compositions of sterilising agents, by irradiation, or by heating. They may also be manufactured in the form of sterile solid compositions, which can be dissolved in a sterile injectable medium immediately before use.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained.

In human therapy, the pharmaceutical compositions according to the invention are particularly useful in the treatment of various forms of gastritis and gastralgia, especially those caused by other medicaments, and in the treatment of ulcerous maladies (e.g. gastric or duodenol ulcers or peptic ulcers).

In human therapy, the doses of the thiazoline derivatives depend on the desired effect and the duration of the treatment; adult doses are generally between 50 and 1000 mg per day, administered orally.

In general, the physician will decide the posology considered appropriate, taking into account the age and weight and other factors intrinsic to the patient being treated.

The following Examples illustrate pharmaceutical compositions according to the present invention.

EXAMPLE 15

Tablets having the following composition are prepared in accordance with the usual technique:
4-methyl-3-(6-methylpyrid-2-yl)-$\Delta^4$-thiazoline-2-thione: 50 mg
starch: 15 mg
precipitated silica: 9.5 mg
magnesium stearate: 0.5 mg.

EXAMPLE 16

Tablets having the following composition are prepared in accordance with the usual technique:
4-methoxymethyl-3-(6-methylpyrid-2-yl)-$\Delta^4$-thiazoline-2-thione: 50 mg
starch: 15 mg
precipitated silica: 9.5 mg
magnesium stearate: 0.5 mg.

We claim:

1. A thiazoline derivative of the formula:

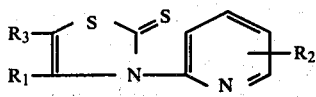

wherein $R_1$ represents hydrogen, an alkyl radical of 1 or 2 carbon atoms or methoxymethyl, $R_2$ represents an alkyl radical of 1 or 2 carbon atoms in the 4-, 5- or 6-position, and $R_3$ represents methyl, or alternatively $R_3$ represents hydrogen and either $R_1$ represents hydrogen, an alkyl radical of 1 through 4 carbon atoms, or an alkoxymethyl radical in which the alkyl moiety contains 1 through 4 carbon atoms and $R_2$ represents an alkyl radical of 1 through 4 carbon atoms in the 4-, 5- or 6-position, or $R_1$ represents cyclopropyl and $R_2$ represents hydrogen.

2. A thiazoline derivative according to claim 1 wherein $R_1$ represents hydrogen or an alkyl radical of 1 through 4 carbon atoms, $R_2$ represents an alkyl radical of 1 through 4 carbon atoms in the 4-, 5- or 6-position, and $R_3$ represents hydrogen.

3. A thiazoline derivative according to claim 1 wherein $R_1$ represents an alkyl radical of 1 through 4 carbon atoms or methoxymethyl, $R_2$ represents an alkyl radical of 1 through 4 carbon atoms in the 4-, 5- or 6-position, and $R_3$ represents hydrogen.

4. A thiazoline derivative according to claim 1 wherein $R_1$ represents an alkyl radical of 1 or 2 carbon atoms or methoxymethyl, $R_2$ represents an alkyl radical of 1 through 4 carbon atoms in the 4-, 5- or 6-position, and $R_3$ represents hydrogen.

5. A thiazoline derivative according to claim 1 which is 4-methyl-3-(4-methylpyrid-2-yl)-$\Delta^4$-thiazoline-2-thione.

6. A thiazoline derivative according to claim 1 which is 4-methyl-3-(6-methylpyrid-2-yl)-$\Delta^4$-thiazoline-2-thione.

7. A thiazoline derivative according to claim 1 which is 3-(6-ethylpyrid-2-yl)-4-methyl-$\Delta^4$-thiazoline-2-thione.

8. A thiazoline derivative according to claim 1 which is 4-ethyl-3-(6-methylpyrid-2-yl)-$\Delta^4$-thiazoline-2-thione.

9. The thiazoline derivative according to claim 1 which is 4-methoxymethyl-3-(6-methylpyrid-2-yl)-$\Delta^4$-thiazoline-2-thione.

10. A thiazoline derivative according to claim 1 which is 4-methyl-3-(6-propylpyrid-2-yl)-$\Delta^4$-thiazoline-2-thione.

11. A thiazoline derivative according to claim 1 which is 4-cyclopropyl-3-(pyrid-2-yl)-$\Delta^4$-thiazoline-2-thione.

12. A thiazoline derivative according to claim 1 which is 3-(6-methylpyrid-2-yl)-$\Delta^4$-thiazoline-2-thione.

13. A thiazoline derivative according to claim 1 which is 4-methyl-3-(5-methylpyrid-2-yl)-$\Delta^4$-thiazoline-2-thione.

14. A thiazoline derivative according to claim 1 which is 4-ethyl-3-(6-ethylpyrid-2-yl)-$\Delta^4$-thiazoline-2-thione.

15. A thiazoline derivative according to claim 1 which is 3-(6-methylpyrid-2-yl)-4-thiazoline-2-thione.

16. A thiazoline derivative according to claim 1 which is 4-butyl-3-(6-methylpyrid-2-yl)-$\Delta^4$-thiazoline-2-thione.

17. A thiazoline derivative according to claim 1 which is 4-isobutyl-3-(6-methylpyrid-2-yl)-$\Delta^4$-thiazoline-2-thione.

18. A thiazoline derivative according to claim 1 which is 4,5-dimethyl-3-(6-methylpyrid-2-yl)-$\Delta^4$-thiazoline-2-thione.

19. An anti gastritis, anti gastralgia or anti ulcer composition which comprises, as active ingredient, an effective amount of a thiazoline derivative as claimed in any one of claims 1 to 18 in association with a pharmaceutically acceptable carrier.

20. A method for the treatment of a patient with gastritis, gastralgia or an ulcerous malady which comprises administering orally to the patient an effective amount of a thiazoline derivative as claimed in any one of claims 1 to 18.

21. A method according to claim 20 in which an amount of from 50 mg to 1000 mg of said thiazoline derivative is administered orally to an adult patient per day.

* * * * *